United States Patent [19]

Lowe et al.

[11] Patent Number: 4,562,157

[45] Date of Patent: Dec. 31, 1985

[54] DIAGNOSTIC DEVICE INCORPORATING A BIOCHEMICAL LIGAND

[75] Inventors: Christopher R. Lowe, Newmarket; Fergus G. P. Earley, Solihull, both of England

[73] Assignee: National Research Development Corporation, London, England

[21] Appl. No.: 614,121

[22] Filed: May 25, 1984

[30] Foreign Application Priority Data

May 25, 1983 [GB] United Kingdom ............... 8314523

[51] Int. Cl.$^4$ ..................... C12M 1/34; G01N 33/54
[52] U.S. Cl. ................................. 435/291; 324/71.1; 435/14; 435/176; 436/526; 436/527; 436/806
[58] Field of Search ............... 436/806, 291, 526, 527; 435/176, 291, 14; 324/71.1

[56] References Cited

U.S. PATENT DOCUMENTS

| | | | |
|---|---|---|---|
| 4,072,576 | 2/1978 | Arwin | 436/806 X |
| 4,238,757 | 12/1980 | Schenck | 436/806 X |
| 4,314,821 | 2/1982 | Rice | 436/806 X |
| 4,444,878 | 4/1984 | Paulus | 436/806 X |
| 4,444,892 | 4/1984 | Malmros | 436/806 X |

OTHER PUBLICATIONS

Chemical Abstracts, 93:88076h (1980).

Breslow, R. et al., J.A.C.S., 96, 5937–5939 (Sep. 4, 1974).

*Primary Examiner*—Sidney Marantz
*Attorney, Agent, or Firm*—Oblon, Fisher, Spivak, McClelland & Maier

[57] ABSTRACT

A device useful in diagnostics in which a biochemical species is attached to the surface of a sensor, especially to the gate of a field effect transistor. In such a "BIO-CHEMFET" it has been a problem to attach two or more biochemical species to the surface of the sensor, especially to the gates of a multi-gated FET. It has now been found possible to bond a group having a photoactivatable function covalently to the sensor surface, photo-expose the resultant modified surface selectively, e.g. through a mask, and bond the biochemical species, e.g. a hapten, antigen, antibody, lectin or enzyme, to the photoactivated function. In this way the biochemical species becomes attached in selected areas only. In view of the success of this technique realized under conditions of miniaturization, the invention makes possible "printed circuits for proteins".

In addition to the device are the process of manufacture thereto, use for diagnostic purposes and a diagnostic kit of the device and a partner capable of binding to the biochemical species.

18 Claims, No Drawings

DIAGNOSTIC DEVICE INCORPORATING A BIOCHEMICAL LIGAND

This invention relates to a device useful in diagnostics in which a biochemical species is attached to the surface of a sensor. An important embodiment relates to a field effect transistor (FET) having a biochemical species attached to the gate thereof (a BIOCHEMFET).

A field effect transistor is a semiconductive device having two spaced apart regions of the same doping polarity, usually n-type, beteen which a potential difference is applied. These regions are connected by a "gate" of insulative material, usually of silica or silicon nitride. Current flows from one of the regions ("the source") to the other region ("the drain") via an induced conducting channel under the gate and is modulated according to the electric potential applied to the gate. Contact of the gate with a material containing charged species alters the electric potential and therefore the value of the source to drain current, which can be measured. Alternatively the source to drain current can be maintained constant by applying an additional potential to the gate and the additional potential necessary for this purpose can be measured.

The FET has been used mainly as an ion-sensitive device, known as an ISFET. The gate region is overlaid with a membrane capable of interacting selectively with ions present in a solution. That is, the membrane adsorbs ions from the solution which alter the electric potential of the membrane and therefore of the gate.

U.S. Pat. No. 4,020,830 (C. C. Johnson, S. D. Moss and J. A. Janata, assignors to the University of Utah) describes ISFETs for use in measuring the concentration of an enzyme or substrate. A second thin film layer or membrane, having an enzyme or substrate immobilized therein is positioned over the ion-selective membrane. When the membrane containing the enzyme, for example, is contacted with a solution containing the substrate, the substrate diffuses into the membrane and reacts with the enzyme. The reaction is accompanied by a net yield or loss of ions. The ion concentration of the underlying ion-selective membrane then changes, thereby affecting its electric potential and giving rise to a measurable change in an electrical signal.

A short review of ISFETs and their application in clinical chemistry and biology is provided by J. Janata, Analytical Proceedings February 1982, pages 65–68.

In another kind of FET mentioned in U.S. Pat. No. 4,020,830, the gate is covered by a membrane or a hydrophobic polymer, e.g. of polyvinyl chloride or polystyrene, to which an antibody or antigen is covalently bound to the surface of the membrane. The covalent bonding of proteins to membranes is described in UK Patent Specification No. 1,527,772 (The University of Utah), in relation to "immunoelectrodes" in which a sensing electrode is surrounded by a sheath of the membrane. In one example, an electrode was coated with polyvinyl chloride, the polyvinyl chloride swelled with a solvent, dried and reacted first with epichlorohydrin and then with the protein Concanavalin A. The reaction of yeast mannan, a polysaccharide precipitated by Concanavalin A was then monitored. In another example rabbit anti-human 7S gamma-globulin antibody was substituted for Concanavalin A and the binding thereof to human 7S gamma-globulin antigen at pH 5 was monitored.

U.S. Pat. No. 4,238,757 (Schenk, assignor to General Electric Company, New York) describes a FET in which a monomolecular layer of a protein, for example an antibody or antigen, is adsorbed onto the top of the insulating layer of the gate. This is a physically attached Langmuir-Blodgett layer. The reaction of the adsorbed antibody with an antigen to be detected affects the charge concentration in the gate and therefore the drain current.

European Patent Specification No. 75353 (Battelle Memorial Institute) describes a method for the determination of a species (analyte) in solution wherein the analyte is made to react with a specific reactant on a waveguide, thus modifying the optical properties of the waveguide, which are measured and compared with standard reference data obtained from calibrating samples of the analyte. The reactant is a protein such as IgG. To attach it the glass is preferably etched in a grating-like pattern with HF. When the IgG (antibody) is introduced, it bonds to the etched areas. An analyte antigen will then be attracted to the IgG. The discontinuity brought about by the pattern will produce a more ordered pattern of scattered light, thus improving the efficiency with which the scattered light is collected in a photomultiplier tube.

U.S. Pat. No. 4,334,480 (Malmros) describes a semiconductor sensor for assay of an analyte in which a specific binding partner for the analyte is absorbed onto a polyacetylene semiconductor. The polyacetylene repeating units $(=CH-CH-)_n$, where n is a large number, have extensive alternating conjugated pi orbitals which provide the semiconductive effect. In order to eliminate "background" variables, two such polyacetylene devices are preferably electrically balanced in the same Wheatstone bridge circuit.

Japanese Patent Application Publication No. 80.10546 (Asahi Glass K.K.) describes a FET immunosensor in which an antibody or antigen is bonded covalently to the insulated gate. Various methods of bonding are proposed. One method is to react the hydroxyl groups of the silica of the gate with gamma-amino propyltriethoxysilane, whereby the ethoxy groups react with the silica and the amino group is left pendant. The amino group is then reacted with the carboxyl group of an antigen or antibody. Another method proposed is to treat the silica surface with thionyl chloride to convert the hydroxyl groups thereof to chlorine atoms and then to react the antigen or antibody, through a carboxyl or amino group thereof, with the chlorinated silica. A more direct method of bonding mentioned involves the reaction of the hydroxyl groups on the silica with carboxyl or hydroxyl groups of an antigen or antibody, thereby forming ester or ether linkages.

To the applicant's knowledge, the prior art has not proposed any solution to the problem of how to attach two or more biochemical species, such as antigens or antibodies, to pre-defined areas on the surface of a "chip". Such a chip could be fabricated as a multi-gated FET, each gate thereby serving as a sensor, and different biochemical species would be attached to the gates. This multi-gated FET could then be used to detect several different species. It would also be possible to attach some standard or reference biochemical species to each chip so as to provide a "control" for each diagnostic test. Although, the prior art mentions the desirability of making such multicomponent devices, see e.g. U.S. Pat. No. 4,020,830, column 11 line 62 to column 12 line 2 and A. U. Ramsing et al., *Analytica Chimica Acta*

118, 45–52 (1980) at page 51, it is not suggested therein how this can be achieved.

*Chemical Abstract* 93, 88076 h (1980), referring to Japanese Patent Application Publication No. 80.24603 (Olympus Optical Co. Ltd.), mentions ISFETs having multiple elements on a single substrate.

U.S. Pat. No. 4,242,096 (Oliviera, assignor to 3Ms Company) describes an assay for antigen using a piezoelectric oscillator pre-coated with an antigen. The oscillator is a small quartz wafer having two metal electrodes deposited thereon. When placed in an oscillator circuit the portion of quartz wafer lying between the electrodes vibrates with a precise natural frequency. The oscillator is coated first with antigen and then with a mixture of an appropriate antibody and an analyte antigen. The antigen coating is provided by adsorption by self-crosslinking it on the surface of the oscillator using glutaraldehyde, or by priming the surface with poly(2-hydroxy-3-dimethylamino-1,4-butane). The same wafer can be provided with a plurality of pairs of electrodes, the portion of crystal between each pair having a different characteristic frequency. The oscillator is then coated with a mixture of antigens each serving as a specific binding partner for a different antibody, whereby the same oscillator can be contacted with several different antibodies and multiple assays carried out using the same quartz crystal. No further details are given and it is not clear how one would selectively coat the electrodes with different antibodies.

It has now been found that it is possible to position individual biochemical species in selected, i.e. predefined, areas of the surface of sensor such as a chip. According to the present invention, the surface of a sensor is modified by attaching to it, by covalent bonding, a group containing a photoactivatable function, exposing the thus modified surface to photoactivating radiation in selected areas only of the surface, to activate the function, and reacting the function thus activated to bond covalently with a biochemical species. The biochemical species will hereinafter be referred to as ligand, a term which denotes merely that it is capable of participating in some form of binding reaction with a suitable partner. The binding may be of the affinity type, e.g. antigen or hapten-antibody or reversible enzyme-substrate, or it may be a chemical binding.

What is novel and inventive herein comprises the idea and the subsequent practical realisation despite the incredibly small scale involved (even a large test chip typically measures only 3 mm×3 mm). that it is possible to use a photoactivation technique to select minutely small areas, most suitably with the aid of a mask, and thereby successfully attach the biochemical ligand covalently in those areas only.

The invention also includes the device so made, which is definable independently of the process of manufacture, as a device which comprises a sensor having a surface to which a group comprising a residue of a biochemical ligand is attached covalently, whereby a physical characteristic of the sensor varies according to whether a binding partner is bound to the ligand, characterized in that the biochemical ligand residue of the group is attached covalently to the surface of the sensor in selected areas only thereof and through a photoactivated covalent linkage.

Also included within the scope of the invention is the use of such a device for assay of a binding partner of the ligand, and a kit useful in diagnostics comprising the device together with at least one binding partner for the biochemical ligand, for testing and/or standardisation of the device.

The invention is particularly applicable to attachment of the group comprising the biochemical ligand residue to a silica surface. A particularly preferred method of attachment is illustrated below, with reference to a silica surface:

(1)

(2)

or

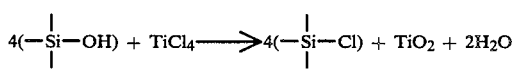

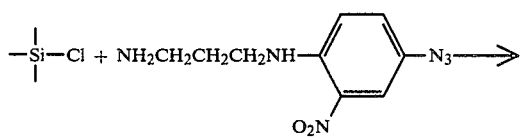

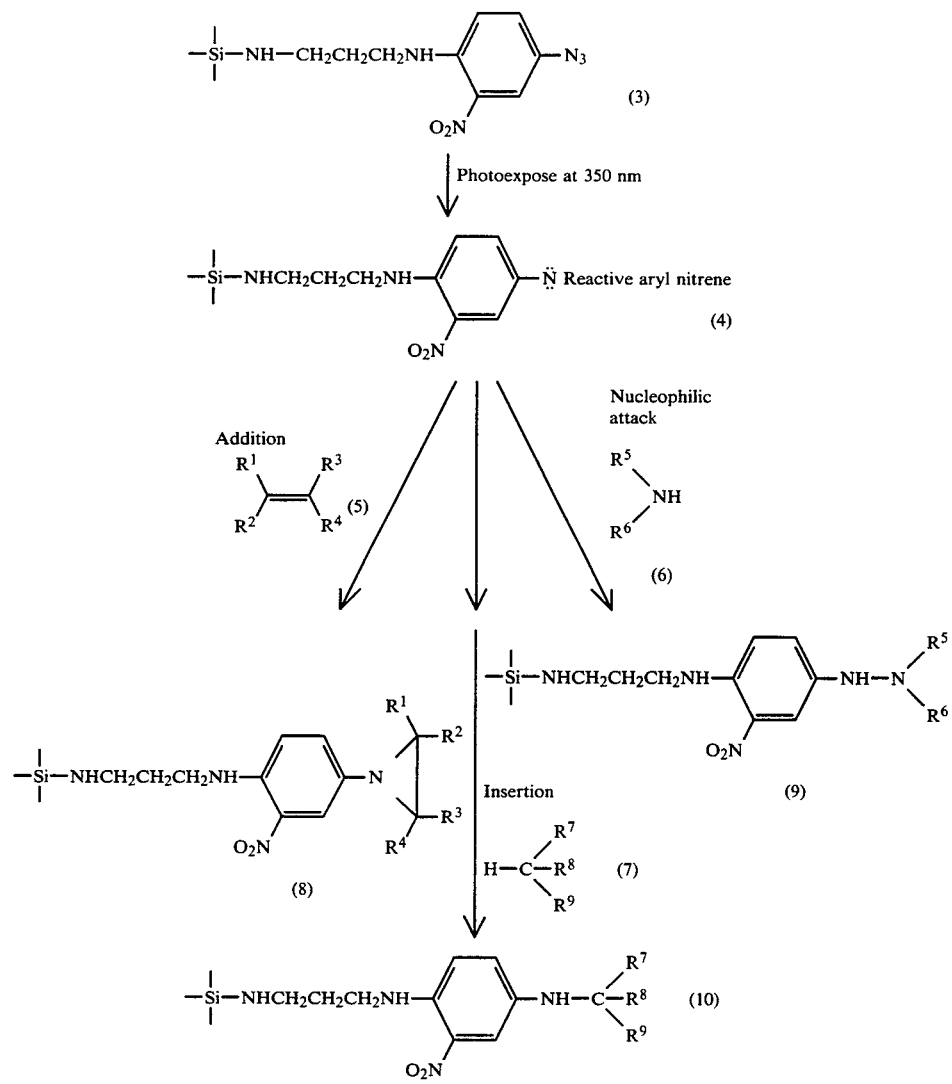

($R^1$, $R^5$ and $R^7$ represent organic groups; $R^2$, $R^3$, $R^4$, $R^6$, $R^8$ and $R^9$ represent organic groups or hydrogen atoms necessary to complete the biochemical ligand molecules (5), (6) and (7).

Reference to the illustrated method, the silica produced by thermal deposition in the manufacture of a chip is mainly in an unreactive form, having such linkages as

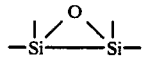

which must first be hydrolysed to a silanol, —Si—OH, form. This can be done by dipping the surface of the chip for about a minute in 10M solution hydroxide, washing with water and then with a hydrophilic organic solvent such as acetone and drying. Alternatively, several hours refluxing in dilute hydrochloric acid produces a hydrophilic surface, although the effect is not as pronounced in the alkali treatment.

The reactive silica surface is then reacted to replace a hydroxyl group by a more reactive function. In the illustrated method this is a chlorine atom, which can be introduced by reaction with any chlorinating agent capable of nucleophilic displacement at a silicon atom of the hydroxyl group, e.g. thionyl chloride or a titanium chloride.

The chlorinated silica surface is then reacted directly with a compound containing a photoactivatable function at one end or in a branch of the molecule and a function at the other end capable of undergoing a nucleophilic displacement of the chlorine atom on the silicon atom. The latter will ordinarily be an amino group as in the illustrated scheme. The photoactivatable function is preferably provided by an aryl azide, e.g. 3-nitro-4-aminophenyl azide, residue. Other examples of residues providing photoactivatable functions are those derived from ethyl 2-diazomalonyl chloride, nitrophenyl ethers of formula

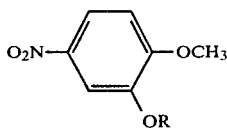

where R is an alkyl group, aromatic ketones as described in *Journal of Biological Chemistry* 249, 3510–3518 (1974), and phosphenyl azides as described by Breslow et al., *Journal of the American Chemical Society*, 96, 5937–9 (1974). Other photoactivatable functions can be provided by the so-called photoaffinity labels, see e.g. Chapter 6, pages 167–179 of the book "Laboratory techniques in biochemistry and molecular biology", Volume 4 Part I: "Chemical Modification of Proteins", by A. N. Glazer, R. J. Delange and D. S. Sigman, general ed. T. S. Work and E. Work, North-Holland Publishing Co. and American Elsevier Publishing Co. Inc. 1975.

A preferred device of the invention has a surface of silica and the biochemical ligand residue is attached to the surface through a group of formula

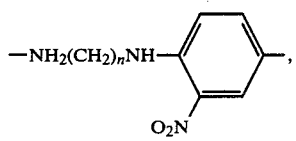

the left-hand end of which is attached to a silicon atom of the surface and the right-hand end of which is attached to the residue of the biochemical ligand, and n is a number from 3 to 12.

Instead of chlorination of the silica and reaction of the chlorinated silica with the group containing the photoactivatable function, it might be desirable to react the silica with a silane, for example allyldimethylchlorosilane, according to the scheme:

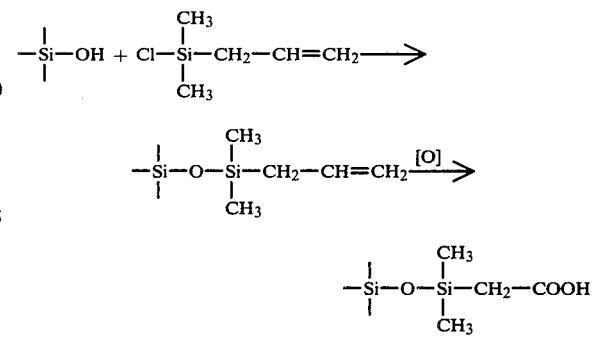

The allyl-terminated siloxane is oxidised, e.g. with potassium permanganate dissolved in benzene and a crown ether, to introduce a carboxyl terminus, which is then reacted with a photoactivator having an amino terminus, forming an amide linkage. Other silanes such as gamma-glycidoxypropylmonomethoxydimethylsilane and cyanopropyldimethylchlorosilane could also be exploited to yield bonded phases capable of subsequent chemical modification for attachment of biochemical ligands.

The following reaction scheme illustrates some methods of modifying a silica surface using a gamma-glycidoxypropyl monomethoxysilane, and attaching thereto a group comprising a biochemical ligand (LR=ligand residue):

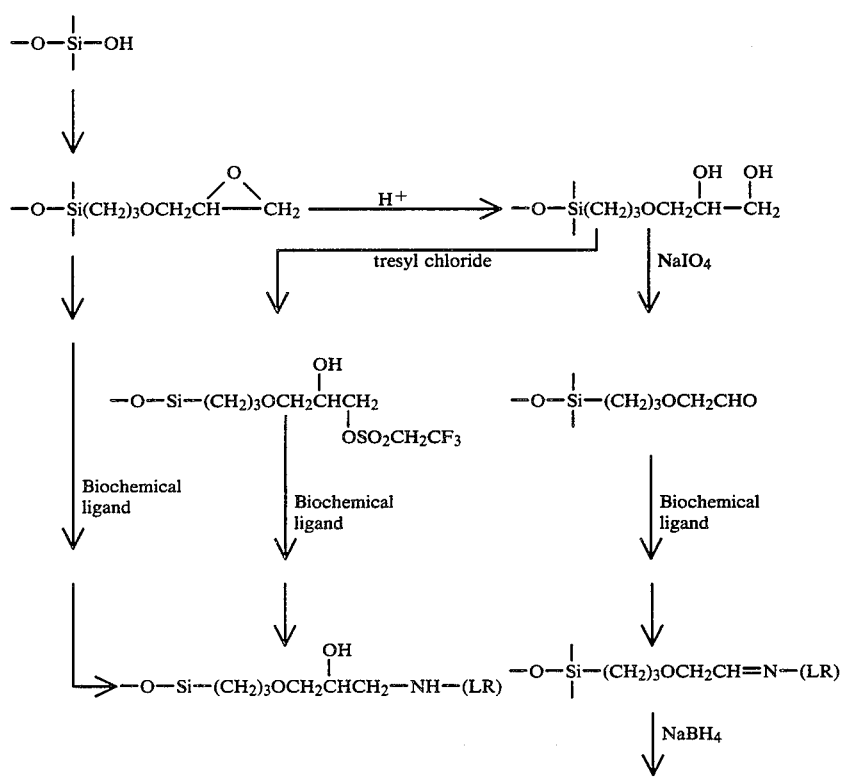

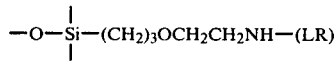

The spacing or bridging arm of the surface-modifying molecule should not be too long, in order to ensure that the sensing function of the device is easily activated by the binding interaction of the biochemical ligand and in order to avoid complications in linking it to the silicon atom. A long carbon-chain spacing arm would create a hydrophobic layer on the silica which might be detrimental, for example, when an enzyme is attached. The enzymic interaction will often be dependent on loss or gain of protons, which will not readily penetrate a hydrophobic layer to reach the sensor surface.

Photoactivation through a mask or screen can be carried out in any manner appropriate for the photoactivating group, i.e. one must choose a radiation, normally in the UV or visible region of the spectrum, to which it is sensitive.

The areas selected by means of the mask for photoactivation can take any appropriate form, depending on how many biochemical ligands are required to be attached. A preferred device is a multi-gated FET having one biochemical ligand attached to each gate and therefore giving an independent signal from other ligands attached to other gates.

For assay purposes a ligand attached to one gate can be left free, i.e. unbound and ready to interact with its partner in the sample to be assayed, while a ligand attached to another gate is blocked from reaction with the binding partner and serves as a control or "reference" gate. In a constant current mode and with a differential amplifier on the same chip, the difference in response of the antigen-sensitive gate and the separate "reference" gate would serve as an internal compensation for any fluctuations in sample composition temperature, pH etc. It is then possible to compare the signals given by the (unbound) ligands, and thereby estimate the amount of binding partner present in the sample.

It is envisaged that the invention can provide a "printed circuit" of a given biochemical ligand, which may have applications outside the diagnostic field, for example, in the development of bio-computers.

The biochemical ligand will normally be a protein and therefore have an amino function. Thus it may be an enzyme, antigen, antibody, receptor protein, other binding protein, or lectin for example. However, it could also be a hapten, co-enzyme, electron mediator or other biologically reactive ligand, particularly one of low molecular weight. Thus, the biochemical ligand could be a sugar or steroid. It may have some other functional group than amino for example a hydroxyl group or carboxyl group in steroid haptens. If the biochemical ligand does not have a group readily reactive with the residue left when the photoactivatable group has been photoactivated, the ligand can normally be further reacted to introduce a more appropriate group.

The silica surface could be replaced by silicon nitride (preferred) or oxynitride or by an oxide of another metal, especially aluminium, titanium (IV) or iron (III) oxides, for example, or any other film, membrane, insulator or semiconductor overlying the device.

The device of the invention need not be based on a FET. Other sensors which can be used include bipolar transistors, semiconductor or other electrodes, piezoelectric crystals, thermoelectric crystals, charge-coupled devices, opto-electronic devices such as integrated optics and waveguide sensors, fibre optic devices, other transducers and magnetic sensors in which a magnetic field strength is measured. Semiconductive devices can contain inorganic semiconductors such as doped silica or organic semiconductors such as polypyrrole. While the physical characteristic sensed is preferably electrical or magnetic, in view of the availability of sensors which amplify changes in electric and magnetic fields, it can in principle be any other physical characteristic, e.g. optical, thermal or the emission or absorption of other radiations.

The following Examples illustrate the invention.

EXAMPLE 1

(1) Synthesis of 4-fluoro-3-nitrophenyl azide 5 grams of 4-fluoro-3-nitroaniline were dissolved in a mixture of 30 ml concentrated HCl and 5 ml water with warming. The solution was filtered and cooled to $-20°$ C. with stirring. (The temperature was maintained between $15°$ and $-20°$ C. during subsequent production and reaction of the diazonium salt.) An ice-cold solution of 2.4 grams of sodium nitrite in 5 ml water was added dropwise with stirring. The mixture was stirred for a further 30 minutes after completion of the addition, then quickly filtered and the resultant diazonium salt solution was returned to the flask. Stirring was continued during dropwise addition of a solution of 2.2 grams of sodium azide in 8 ml ice-cold water. After completion of this addition, the mixture was allowed to warm and the product was collected by filtration and washed with water. After drying, the product was recrystallised from petroleum ether.

(2) Synthesis of N-(4-azido-2-nitrophenyl)-1,3-diaminopropane 2.5 ml (30 mM) 1,3-diaminopropane was dissolved in 25 ml ethanol. To this solution, was added a solution of 1.82 g (10 mM) 4-fluoro-3-nitrophenyl azide in 25 ml ethanol. The addition was performed dropwise with stirring. The mixture was stirred at room temperature for 16 hours. After this time, 150 ml of water were added and the pH adjusted to between 1 and 2 with concentrated HCl. This solution was filtered to remove the disubstituted amine, cooled on ice and the product was precipitated by the slow addition of concentrated aqueous ammonia with stirring. The product was collected by filtration of the cold mixture, washed with ice-cold water and dried in vacuo.

(3) Pre-treatment of the silica surface

Silicon semiconductor slices having a surface layer of silica were grown thermally and divided into 3 mm square chips. The silica surfaces were hydrolysed by dipping the slices in 10M sodium hydroxide for 1 minute. The slice and solution were not agitated. This treatment was followed by extensive washing in water and slow drying in a stream of nitrogen or argon. This yielded a very hydrophilic surface.

(4) Coupling of N-(4-azido-2-nitrophenyl)-1,3-diaminopropane to the silica surface Absorbed water on the silica surface was first removed by heating the slices to 105° C. under high vacuum. The slices were then immersed in freshly distilled thionyl chloride. The vessel was sealed and allowed to stand at room temperature for 24 hours. From this stage until completion of coupling of the enzyme, water was rigorously excluded. After 24 hours, excess of thionyl chloride was poured off the slices, the vessel was evacuated and heated to 150° C. under high vacuum to remove adsorbed thionyl chloride, hydrogen chloride and sulphur dioxide from the surface. After cooling, a saturated solution of N-(4-azido-2-nitrophenyl)-1,3-diaminopropane in dry tetrahydrofuran was added and allowed to react in the drak at 40° C. for 24 hours.

(5) Light-dependent coupling of beta-galactosidase to the surface

All operations were performed under red safety light. The slices were removed from the above-mentioned reaction solution and washed in tetrahydrofuran and water and covered with about 1 microliter of a solution of *E. coli* beta-galactosidase, Sigma grade VIII, activity about 1,000 units/ml in 0.1M sodium phosphate buffer of pH 7.5 containing 0.5M NaCl. The enzyme solution was kept on ice before use. The slice was exposed to light from a high pressure mercury vapour lamp (125 watts) through a mask. The incident light was first caused to be reflected from a plastic mirror which absorbs the far ultra-violet light. The mask was of aluminium having a pattern consisting of 5 circular holes arranged in a cruciform layout. The exposure time was 1 minute, after which the slice was washed extensively in ice-cold buffer (0.1M sodium phosphate, pH 7.5 containing 0.5M sodium chloride. The slice was stored in this buffer and could then be exposed to normal lighting.

(6) Assay for beta-galactosidase activity

A saturated solution of 4-methylumbelliferyl beta-D-galactopyranoside was prepared in the above buffer and spread on the surface of the exposed slice. The slice was placed in a dark box under a short-wave ultra-violet lamp. Care was taken not to agitate the slice. After several minutes, blue florescence was observed, the intensity of which reproduced the pattern of 5 holes of the mask. The fluorescence is due to the release of 4-methylumbelliferone from the hydrolysis of 4-methylumbelliferyl-beta-D-galactopyranoside by beta-galactosidase.

EXAMPLE 2

Example 1 was repeated, using an alternative procedure for the chlorination of the silica surface. After pre-treatment of the slices and drying as described previously, the slices were placed in 10 ml dry toluene, to which was added 0.5 ml titanium (IV) chloride. The reaction was allowed to proceed overnight. The slices were then removed, washed with dry toluene and placed in a tetrahydrofuran solution of N-(4-azido-2-nitrophenyl)-1,3-diaminopropane as described previously. Again, great care was taken to exclude moisture.

EXAMPLE 3

(1) Pre-treatment of the silica surface

The precedure of Example 1, stage (3) was repeated, using a chip coated with silicon nitride instead of silica.

(2) Reaction of allyldimethylchlorosilane with the surface of the chip

The slices were heated to 150° C. under high vacuum to remove absorbed water on their surfaces. They were then immersed in 10 ml of sodium-dried toluene containing 1 ml of allyldimethylchlorosilane and 0.1 ml dry pyridine. The reaction vessel was filtered with a condenser and drying tube to exclude moisture and the toluene is refluxed for approximately 3 hours. The slices were then washed exhaustively in benzene, followed by toluene and finally acetone. The hydrophobicity of the resultant surfaces indicated that the reaction had been successful.

(3) Oxidation of the allyl group 10 mg of the macrocyclic polyether known as "18-crown-6" was dissolved in 100 ml benzene. The solution was shaken vigorously with a concentrated aqueous solution of potassium permanganate until the purple colour of the benzene reacted a maximum intensity. The benzene layer was separated and filtered through a 2 micrometer "Millipore" (Registered Trade Mark) filter and applied to the surface of the slices. After 2 hours at room temperature the slices were washed exhaustively in benzene, followed by toluene and finally acetone. The surface reverted to a hydrophilic character, indicating the presence of the desired carboxylic acid group in place of the terminal vinyl part of the allyl group.

(4) Coupling of the N-(4-azido-2-nitrophenyl)-1,3-diaminopropane to the surface

The slices were washed in dry tetrahydrofuran and subsequently incubated with 1-ethyl-3-(3-dimethyl aminopropyl)carbodiimide (0.5 mg/ml in dry tetrahydrofuran) for 1 hour at 25° C. The slices were washed exhaustively with dry tetrahydrofuran and incubated with a saturated solution of N-(4-azido-2-nitrophenyl)-1,3-diaminopropane in dry tetrahydrofuran in the dark at 40° C. for 24 hours.

(5) Light-dependent coupling of beta-galactosidase to the surface (6) Assay for beta-galactosidase activity These steps were carried out as in Example 1.

EXAMPLE 4

Modified and unmodified silicon chips (4 mm×4 mm) prepared as described above were placed in PTFE housing and held firmly by rubber O-rings. Electrical contact to the rear face of the chip was achieved by grinding a small amount of gallium/indium eutectic in with a diamond pen in order to remove the $SiO_2$ layer grown during storage and contacting with a brass/silver rod to which electrical contact was made in the normal way.

An Ag/AgCl microreference electrode for use with silicon chips was fabricated by pulling out 3 mm soda glass tubing to a fine capillary 0.2 mm diameter. The capillary was sealed at the fine end with a plug of 2% (w/v) agarose saturated with KCl to act as a salt bridge and sealed at the other with an Ag/AgCl wire in saturated AgCl/KCl. The potential of the microreference electrode was tested versus SCE at various pH values using a high input impedance ($10^4$ ohms) Keithley Model 642 electrometer. It was found that the drift in the Ag/AgCl microreference electrode was less than 1 mV per decade in pH and was therefore considered acceptable to act as a reference electrode for the modified chips.

Sodium acetate/sodium tetraborate buffers of equi-ionic strength but different pH values were used at 20.5° C. in order to assess the pH response of $SiO_2$ and $Si_3N_4$ coated chips both before and after surface silanization and derivatization as described above. The pH response of the electrode at constant ionic strength was substantially linear, giving a slope of approximately 35 mV per pH unit over the pH range 3.5 to 7 for $Si_3N_4$-coated chips and approximately 16 mV per pH unit over the pH range 2 to 9 for $SiO_2$-coated chips. The linearity was unaltered on subsequent silanization. This observation opens the way to covalently bonding such enzymes as penicillinase to silanized oxide, oxynitride or nitride with retention of the pH response and thus of fabricating an enzyme-coated FET.

EXAMPLE 5

Example 3, steps (1) to (6) were repeated except that alkaline phosphatase was used in place of beta-galactosidase and 4-methyl umbelliferyl phosphate was used as the substrate generating fluorescence (by hydrolysis of the phosphate by alkaline phosphatase).

We claim:

1. A device for diagnostics comprising:
   a sensor having a surface to which a biochemical ligand is attached covalently, in a manner effective to cause a physical characteristic of the sensor to vary according to whether a binding partner becomes bound to the ligand, wherein the biochemical ligand is attached covalently to the surface of the sensor in selected areas only thereof and through a photoactivated covalent linkage.

2. A device according to claim 1, wherein the biochemical ligand is an antigen or hapten and a physical characteristic of the sensor varies according to whether or not an antibody becomes bound to the antigen or hapten.

3. A device according to claim 1, wherein the biochemical ligand is an antibody and a physical characteristic of the sensor varies according to whether or not an antigen or hapten becomes bound to the antibody.

4. A device according to claim 1, wherein the biochemical ligand is an enzyme and a physical characteristic of the sensor varies according to whether or not a substrate becomes bound to the enzyme.

5. A device according to claim 1, wherein the biochemical ligand is a co-enzyme, steroid, sugar, electron mediator or other low molecular weight biochemical.

6. A device according to claim 1, wherein the surface of the sensor is of an inorganic oxide, oxynitride or nitride.

7. A device according to claim 6, wherein the surface is of silica or silicon nitride.

8. A device according to claim 6, wherein the surface is of iron (III) oxide and the sensor measures magnetic field strength.

9. A device according to claim 6, wherein the surface is of silica or silicon nitride and the sensor is a field effect transistor.

10. A device according to claim 1, wherein the photoactivated covalent linkage is provided by the photolysis of an aryl azide group.

11. A device according to claim 10, wherein the surface is of silica and the biochemical ligand is attached to the surface through a group of formula:

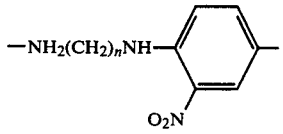

the left bond is attached to a silicon atom of the surface and the right bond is attached to the biochemical ligand, and n is an integer from 3 to 12.

12. A device according to claim 1, wherein the sensor is a field effect transistor, the surface is of silicon nitride and the photoactivated covalent linkage is an aryl azide group.

13. A process of preparing the device claimed in claim 1, which process comprises modifying the surface of the sensor by attaching to it by covalent bonding a group containing a photoactivatable function, exposing the thus modified surface to photoactivating radiation in selected areas only of the surface to activate the photoactivatable function and reacting the photoactivatable function thus activated to bond covalently the biochemical ligand.

14. A process according to claim 13, wherein the modified surface is exposed to the photoactivating radiation through a mask.

15. A process according to claim 13, wherein different biochemical ligands are attached to different areas of the same surface.

16. A process according to claim 13, wherein the sensor is a field effect transistor, the surface is of silicon nitride and the photoactivatable function is an aryl azide group.

17. A kit for diagnostics comprising the device claimed in claim 1 and at least one binding partner for the biochemical ligand for testing or standardisation of the device.

18. The device of claim 1 wherein said physical characteristic is an electrical, magnetic, optical or thermal characteristic.

* * * * *